April 3, 1934. H. I. SHOTWELL Plant Pat. 90
APPLE
Filed Jan. 25, 1933
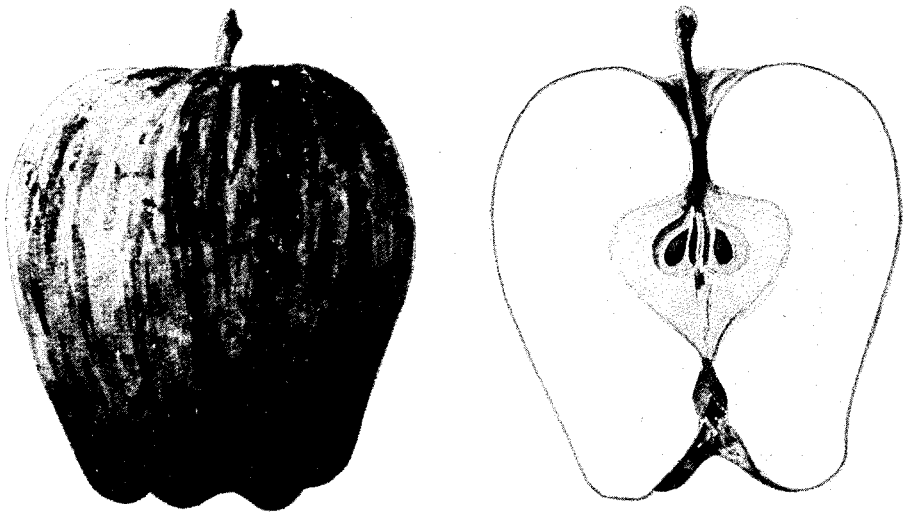
INVENTOR
Harry I. Shotwell
By Orville M. Kile
Plant Patent Agent Patented Apr. 3, 1934

Plant Pat. 90

UNITED STATES PATENT OFFICE

90

APPLE

Harry I. Shotwell, Wenatchee, Wash.

Application January 25, 1933, Serial No. 653,504

1 Claim. (Cl. 47—62)

My invention relates to improvements in apples of the type depending on color and earliness of coloring for a portion of their commercial value. The objects of my improvements are, first, to provide an apple of the well-known Delicious type which will color up about two weeks earlier than the Delicious and therefore be ready to reach the earlier and higher priced markets; and, second, to secure on each tree a higher percentage of fruits having the desired high coloring.

This new variety first occurred as a bud sport or mutation on a Delicious tree in my orchard located about four miles north of Wenatchee, Washington. One entire limb produces apples identical with those of the remainder of the tree except as to date of coloring and percentage of fruit attaining the desired high degree of coloration, also with the further exception of darker final color and striping not as pronounced or prominent. The shape, size, flavor and texture of the fruit and general growing qualities and appearance of the tree are identical with the well-known common Delicious variety.

Trees grown and developed from scions taken from the original bud sport limb by me, produce fruit identical in characteristics with that grown on the original limb.

The accompanying illustration shows a typical specimen of this variety in full colored side view and in vertical cross section. However, it must be understood that no painting or drawing can disclose several of the more important features on which I base my claims to patent protection.

This variety may be described fully and completely by stating that it has all the standard and well known characteristics of the Delicious variety of apples; except, (1) it colors up about two weeks earlier than the Delicious when grown under similar soil and climatic conditions; (2) it produces a much higher percentage of highly colored apples per tree—usually 3 to 4 times as many—; (3) is has a deeper darker shade of red than the typical Delicious; (4) the striping is less pronounced; and (5) this new variety is specked with white or nearly white dots or specks whereas the typical Delicious variety has specks of a yellowish tint.

*Tree* is larger, vigorous and spreading in character, hardy and productive.

*Fruit* is large, oblong conic in shape, ribbed and has five knob-like protrusions at the calyx end; stem long, medium thick; cavity deep, broad and often furrowed; calyx medium, nearly closed; basin deep, wide abrupt and furrowed; skin smooth, medium thick and tenacious; core medium size, axile closed with clasping calyx segments; seeds plump, medium size, brown; flesh yellowish, firm, tender, juicy, aromatic; flavor sub-acid, very pleasant.

*Color* dark red, being approximately "Carmine" (Ridgeway's Color Standards and Nomenclature, Plate I) in the predominant color effect with certain portions shading out to lighter and brighter reds while other portions are darker, approaching "Oxblood red" or "Garnet brown," as shown in Ridgeway's Color Standards and Nomenclature. While these major color differences are in general distributed over the apple in several well defined areas, there is in addition some variation in shades distributed in such a way as to produce an axially striped effect, although this is much less marked than in the typical common Delicious apple. Small whitish dots speck the surface in profuse but irregular fashion.

I claim:

The variety of apple of "Delicious" type herein described and illustrated characterized particularly by its earlier coloring, its deeper darker red coloring, its much higher percentage of highly colored fruit produced per tree, its less prominent stripes, and the whitish specks on its surface.

HARRY I. SHOTWELL.